United States Patent
Ho (10) Patent No.: US 11,551,811 B2
(45) Date of Patent: Jan. 10, 2023

(54) SURGICAL ITEM MANAGING METHOD AND SURGICAL ITEM MANAGING SYSTEM FOR SMART OPERATING ROOM

(71) Applicant: AI Bioelectronic Healthtech Co., Ltd., Taoyuan (TW)

(72) Inventor: Yen-Yi Ho, Taoyuan (TW)

(73) Assignee: AI Bioelectronic Healthtech Co., Ltd., Taoyuan (TW)

( * ) Notice: Subject to any disclaimer, the term of this patent is extended or adjusted under 35 U.S.C. 154(b) by 349 days.

(21) Appl. No.: 16/997,150

(22) Filed: Aug. 19, 2020

(65) Prior Publication Data
US 2021/0407659 A1 Dec. 30, 2021

(30) Foreign Application Priority Data
Jun. 30, 2020 (TW) ................. 109122075

(51) Int. Cl.
| | |
|---|---|
| *G16H 40/20* | (2018.01) |
| *H04B 17/318* | (2015.01) |
| *G06T 7/70* | (2017.01) |
| *G16H 40/40* | (2018.01) |
| *G16H 40/63* | (2018.01) |
| *A61B 5/00* | (2006.01) |

(Continued)

(52) U.S. Cl.
CPC ........... *G16H 40/20* (2018.01); *A61B 5/0046* (2013.01); *A61B 5/0077* (2013.01); *A61B 5/746* (2013.01); *G06K 19/0723* (2013.01); *G06T 7/70* (2017.01); *G08B 21/24* (2013.01); *G16H 40/40* (2018.01); *G16H 40/63* (2018.01); *H04B 17/318* (2015.01); *G06T 2207/10016* (2013.01); *G06T 2207/30004* (2013.01); *G06T 2207/30196* (2013.01)

(58) Field of Classification Search
CPC ........ G16H 40/20; G16H 40/40; G16H 40/63; G16H 30/20; G16H 20/40; A61B 5/0046; A61B 5/0077; A61B 5/746; G06K 19/0723; G06T 7/70; G06T 2207/10016; G06T 2207/30004; G06T 2207/30196; G08B 21/24; H04B 17/318
See application file for complete search history.

(56) References Cited

U.S. PATENT DOCUMENTS

| | | | | |
|---|---|---|---|---|
| 2002/0067263 A1* | 6/2002 | Tafoya | ................... | A61B 90/98 340/8.1 |
| 2005/0131397 A1* | 6/2005 | Levin | ..................... | G06K 17/00 606/1 |

(Continued)

FOREIGN PATENT DOCUMENTS

EP 3505113 A1 12/2018

*Primary Examiner* — Ryan W Sherwin
(74) *Attorney, Agent, or Firm* — Alan D. Kamrath; Karin L. Williams; Mayer & Williams PC (57) ABSTRACT

A surgical item managing method for use in a smart operating room to manage a surgical item used during a surgical procedure is provided. The surgical item includes a flexible RFID tag. The method includes the steps of: obtaining an information about a position of the flexible RFID tag; photographing a patient to obtain a position of the patient; determining if the position of the flexible RFID tag and the position of the patient overlap, to determine if the position of the flexible RFID tag is in the body of the patient; and giving a warning when the position of the flexible RFID tag is in the body of the patient.

13 Claims, 5 Drawing Sheets

(51) Int. Cl.
G06K 19/07 (2006.01)
G08B 21/24 (2006.01)

(56) References Cited

U.S. PATENT DOCUMENTS

| | | | |
|---|---|---|---|
| 2007/0125392 A1* | 6/2007 | Olson, Jr. | A61B 90/90 |
| | | | 128/899 |
| 2008/0081982 A1* | 4/2008 | Simon | A61B 34/25 |
| | | | 600/407 |
| 2008/0200926 A1 | 8/2008 | Verard et al. | |
| 2009/0317002 A1* | 12/2009 | Dein | A61B 90/90 |
| | | | 340/568.1 |
| 2014/0275981 A1 | 9/2014 | Selover et al. | |
| 2017/0095315 A1 | 4/2017 | van der Weide et al. | |
| 2020/0312464 A1* | 10/2020 | Shiraga | G16H 30/20 |
| 2020/0395118 A1* | 12/2020 | Codd | G16H 40/40 |
| 2022/0246288 A1* | 8/2022 | Yavari | G16H 40/20 |

* cited by examiner

SURGICAL ITEM MANAGING METHOD AND SURGICAL ITEM MANAGING SYSTEM FOR SMART OPERATING ROOM

BACKGROUND OF THE INVENTION

Field of the Invention

The present disclosure relates to a surgical item managing method and a surgical item managing system for an operating room and, more particularly, to a surgical item managing method and a surgical item managing system for an operating room to prevent retained surgical items (RSIs).

Description of the Prior Art

Surgery is performed on patients, using surgical instruments like scalpels, artery forceps, and suturing instruments, as well as consumables like gauze and cotton pads. Conventionally, a surgical procedure involves dissecting the tissue in the vicinity of a lesion, cutting the lesion, suturing the lesion to stem bleeding from the lesion, removing all surgical instruments and consumables from the patient's body, and finally suturing the dissected tissue.

However, at the end of surgery, some surgeons who are busy or tired forget to remove from their patients' bodies surgical instruments and consumables (retained surgical items, RSIs). RSIs are harmful to human tissue, posing a threat to medical safety and patients' health.

RSIs have a global incidence of 10% and are a major category of medical negligence. Therefore, it is necessary to provide a method and device for preventing RSIs.

SUMMARY OF THE INVENTION

It is an objective of the present disclosure to provide a surgical item managing method for a smart operating room to prevent retained surgical items (RSIs).

In order to achieve the above and other objectives, the present disclosure provides a surgical item managing method for a smart operating room, for use by a surgical item managing system for the smart operating room to manage a surgical item used during a surgical procedure, the surgical item including a flexible RFID tag, the surgical item managing method including the steps of: obtaining a tag position of the flexible RFID tag; taking an image of a patient, so as to obtain an image position of the patient; determining whether a position of the flexible RFID tag and the image position of the patient overlap, so as to determine whether the surgical item corresponding to the flexible RFID tag is in the patient's body; and sending a warning when the surgical item is in the patient's body. Therefore, the surgical item managing method is effective in sending position-related data to a blockchain system of an external network to record and track the entire surgical procedure.

According to an embodiment of the present disclosure, the step of obtaining the tag position of the flexible RFID tag further includes: scanning the flexible RFID tag and receiving a plurality of return signals.

According to an embodiment of the present disclosure, the step of obtaining the tag position of the flexible RFID tag further includes: computing the tag position of the flexible RFID tag according to levels of signal strength of the return signals.

According to an embodiment of the present disclosure, the surgical item managing method for a smart operating room further includes: transmitting data about the position of the flexible RFID tag to an external computer or a blockchain network.

According to an embodiment of the present disclosure, the flexible RFID tag carries a transportation history, and the surgical item managing method for a smart operating room further includes: recording the transportation history in a blockchain network. Therefore, surgical record cannot be tampered with.

Another objective of the present disclosure is to provide a surgical item managing system for a smart operating room to prevent retained surgical items (RSIs).

In order to achieve the above and other objectives, the present disclosure provides a surgical item managing system for use in a smart operating room to manage a surgical item used during a surgical procedure. The surgical item includes a flexible RFID tag. The surgical item managing system for a smart operating room includes an RFID tag reader/writer, a video recording module, a processing module and a warning module. The RFID tag reader/writer scans the flexible RFID tag. The video recording module takes images of a patient to obtain a position of the patient. The processing module is in signal connection with the RFID tag reader/writer and a video recording module. The processing module computes a position of the flexible RFID tag according to a data which the RFID tag reader/writer acquires by scanning the flexible RFID tag and determine whether a position of the flexible RFID tag and the image position of the patient overlap, so as to determine whether the position of the flexible RFID tag is in the patient's body. The warning module is in signal connection with the processing module. The warning module sends a warning signal when the processing module determines that the position of the flexible RFID tag is in patient's body.

According to an embodiment of the present disclosure, the RFID tag reader/writer scans the flexible RFID tag and receives a plurality of return signals.

According to an embodiment of the present disclosure, the processing module computes the position of the flexible RFID tag according to levels of signal strength of the return signals.

According to an embodiment of the present disclosure, the surgical item managing system for a smart operating room further includes a network module. The network module is in signal connection with the RFID tag reader/writer. The network module transmits data about the position of the flexible RFID tag to an external computer or a blockchain network.

According to an embodiment of the present disclosure, the surgical item managing system for a smart operating room further includes a blockchain tracking module. The blockchain tracking module is in signal connection with the RFID tag reader/writer. The blockchain tracking module records a transportation history in a blockchain network.

According to an embodiment of the present disclosure, the surgical item further includes at least one surgical instrument and at least one surgical consumable.

DETAILED DESCRIPTION OF THE EMBODIMENTS

The implementation of the present disclosure is illustrated by preferred, specific embodiments to enable persons skilled in the art to easily understand the other advantages and effects of the present disclosure by referring to the disclosure contained therein.

Figure 1:
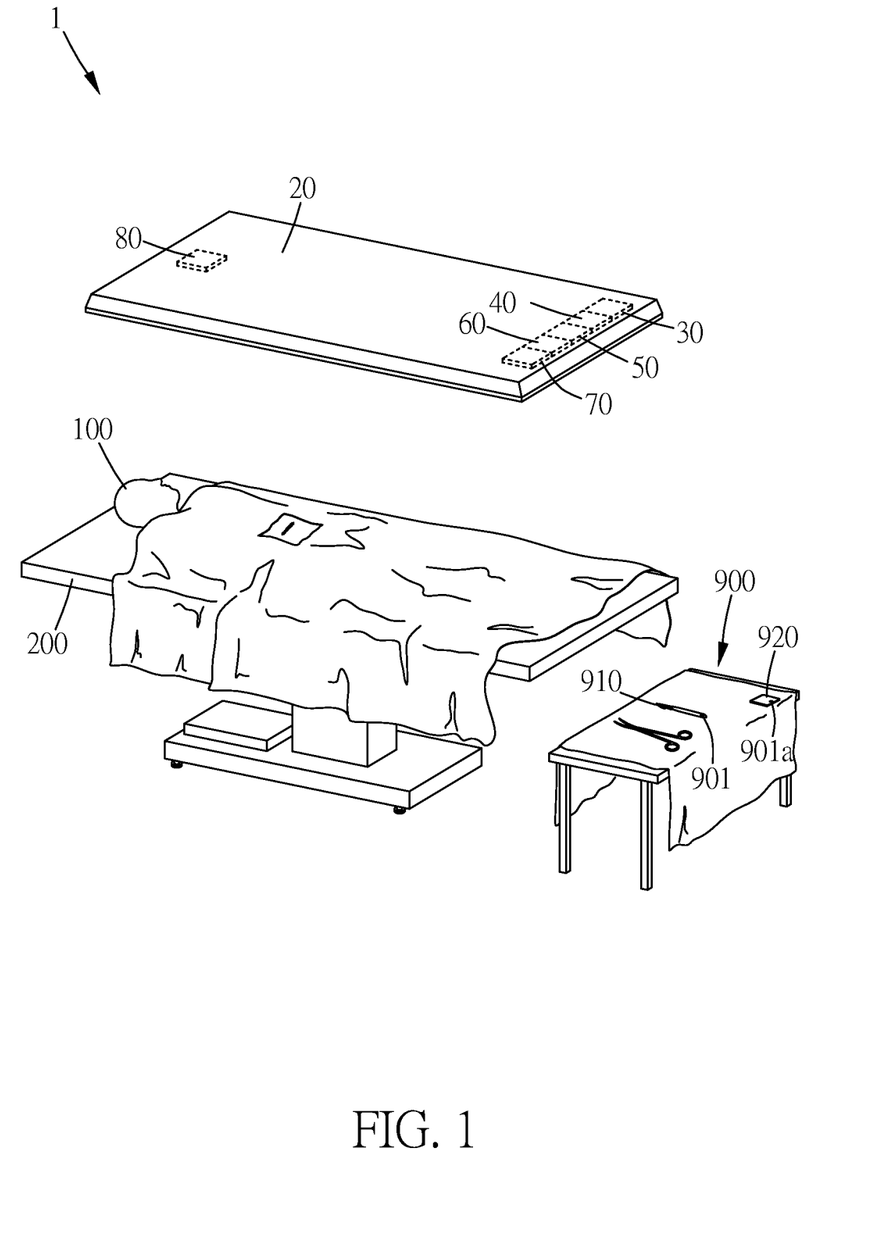
FIG. 1 is a schematic view of a patient on an operating table, a surgical item managing system for a smart operating room, and a surgical item according to an embodiment of the present disclosure.
Figure 2:
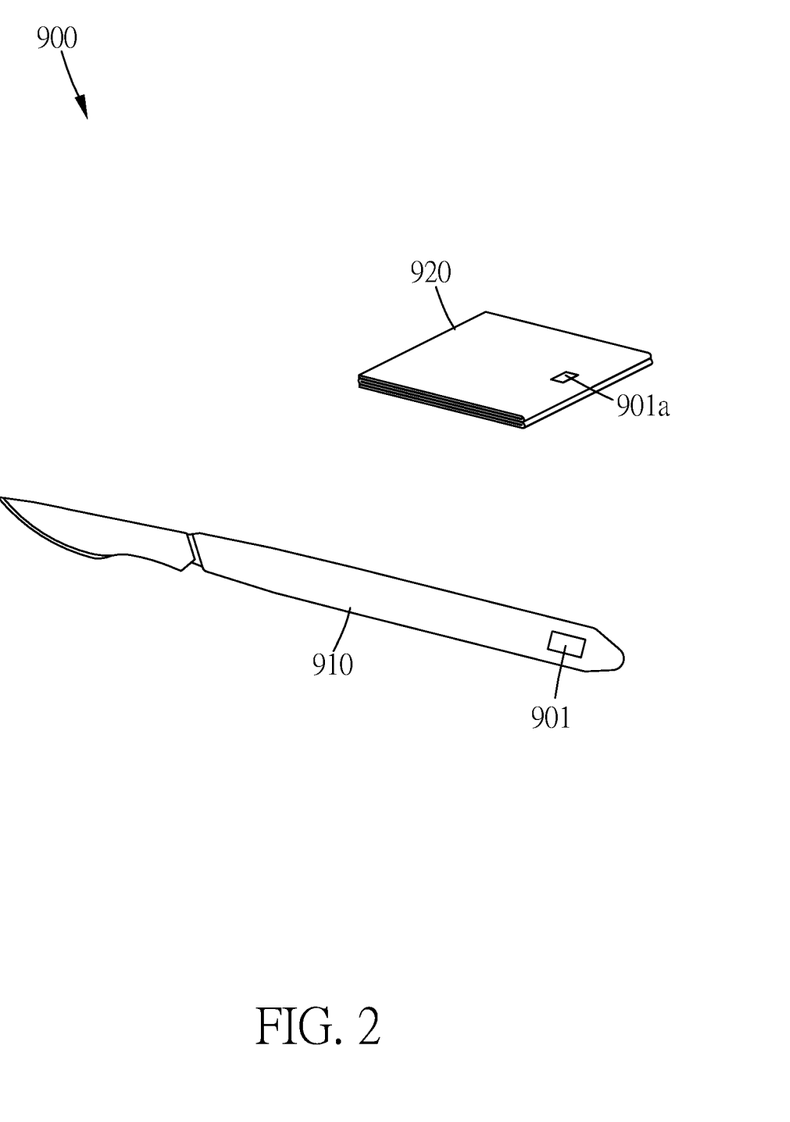
FIG. 2 is a schematic view of the surgical item and flexible RFID tags according to an embodiment of the present disclosure.
Figure 3:
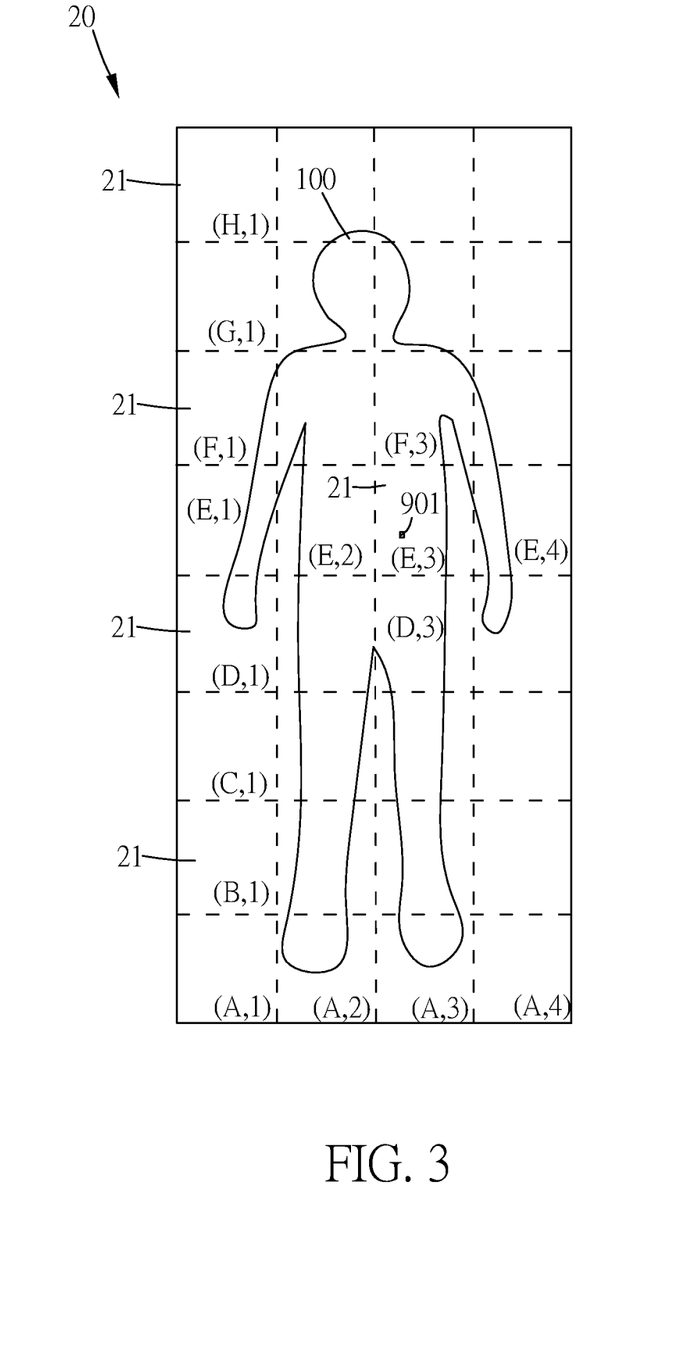
FIG. 3 is a schematic view of read regions of an RFID tag reader/writer according to an embodiment of the present disclosure.
Figure 4:
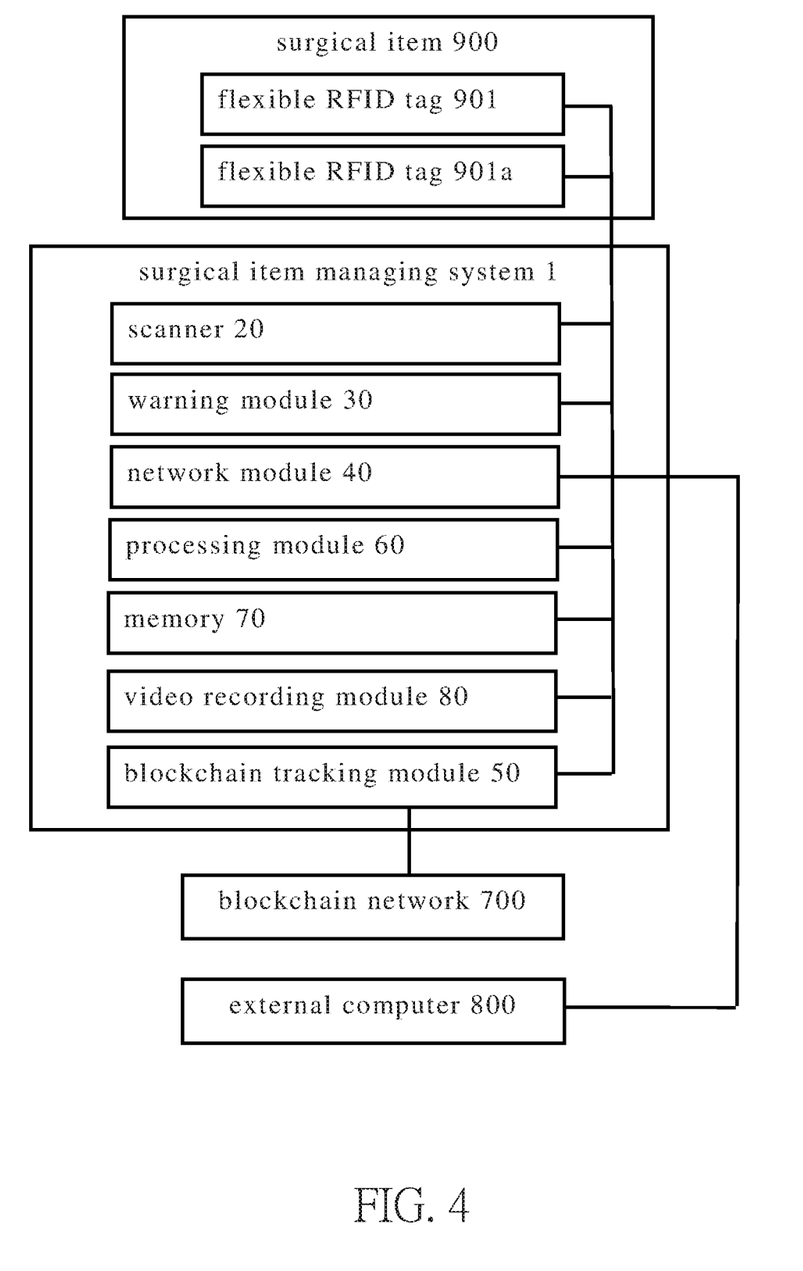
FIG. 4 is a block diagram of the surgical item managing system for a smart operating room, a blockchain network and an external computer according to an embodiment of the present disclosure.
Figure 5:
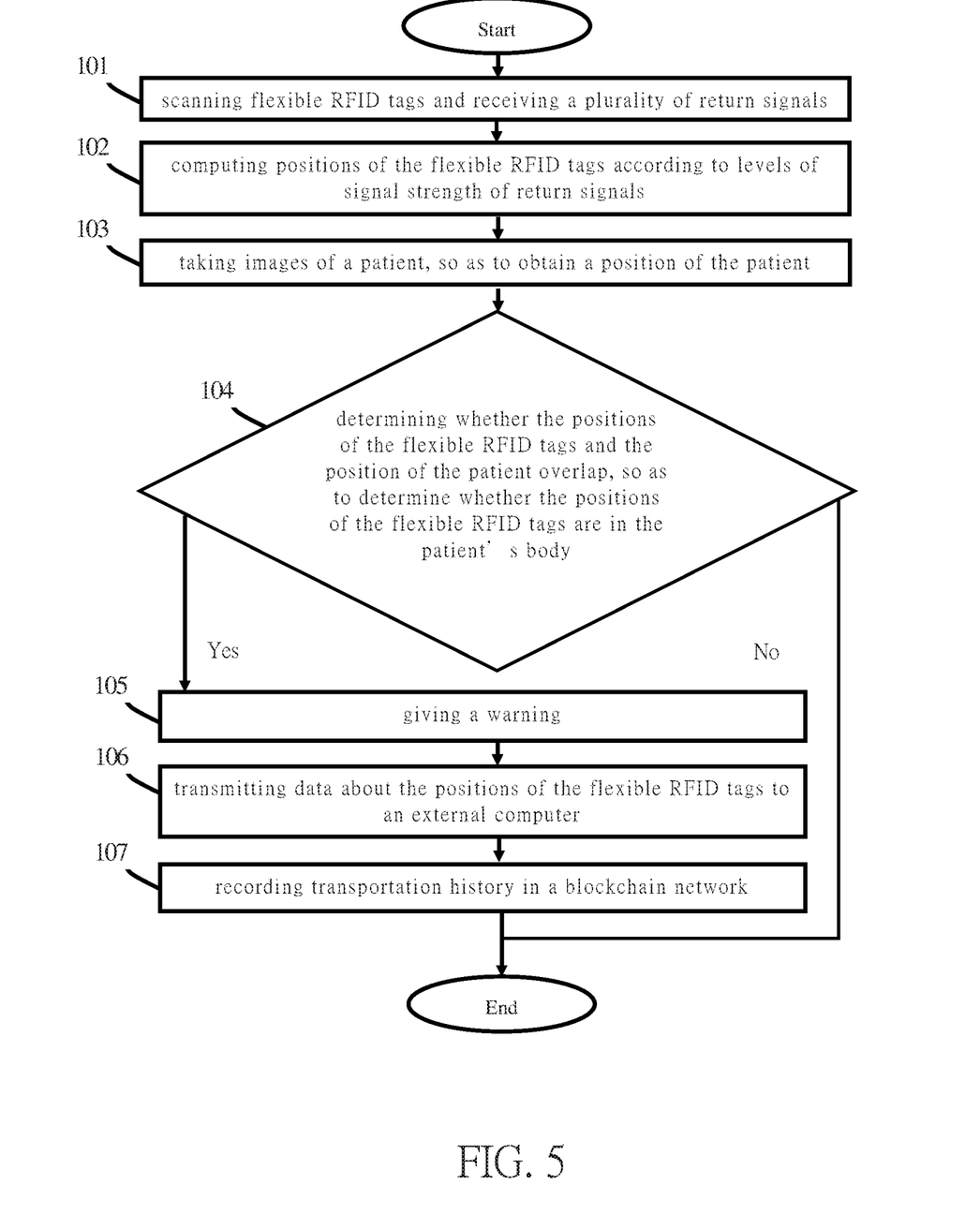
FIG. 5 is a flowchart of a surgical item managing method for a smart operating room according to an embodiment of the present disclosure.

Referring to FIG. 1 through FIG. 5, a surgical item managing system for a smart operating room and a surgical item managing method for the smart operating room are provided in an embodiment of the present disclosure. FIG. 1 is a schematic view of a patient on an operating table, a surgical item managing system for a smart operating room, and a surgical item according to an embodiment of the present disclosure. FIG. 2 is a schematic view of the surgical item and flexible RFID tags according to an embodiment of the present disclosure. FIG. 3 is a schematic view of read regions of an RFID tag reader/writer according to an embodiment of the present disclosure. FIG. 4 is a block diagram of the surgical item managing system for a smart operating room, a blockchain network and an external computer according to an embodiment of the present disclosure. FIG. 5 is a flowchart of a surgical item managing method for a smart operating room according to an embodiment of the present disclosure.

As shown in FIG. 1 through FIG. 4, in an embodiment of the present disclosure, a surgical item managing system 1 for a smart operating room manages a surgical item 900 is used during a surgical procedure to prevent the surgical item 900 from being left behind in the body of a patient 100 (also known as "retained surgical item (RSI)"), so as to reduce medical negligence and medical disputes, prevent reinfection, and reduce the required healthcare staff. The system 1 is a necessary post-operative facility for use in a smart operating room. The patient 100 lies on an operating table 200 while receiving a surgical operation. The surgical item 900 is, for example, a surgical instrument kit whose package comes with a positioning chip and is made of flexible, biodegradable plastic. The surgical item 900 includes two flexible RFID tags 901, 901a, a surgical instrument 910 and a surgical consumable 920. The surgical instrument 910 is, for example, a scalpel, whose handle is made of biodegradable plastic. The surgical consumable 920 is, for example, a gauze, which is made of biodegradable plastic. However, the numbers of the surgical instrument 910 and surgical consumable 920 are not limited thereto but are subject to changes, for example, are changed to at least one. Furthermore, the surgical instrument 910 may also be scissors, clamp, retractor, artery forceps, or suturing instrument. Likewise, the surgical consumable 920 may also be fabric, surgical sponge, cotton pad or the like.

In an embodiment of the present disclosure, the two flexible RFID tags 901, 901a are sensing chips disposed on the surgical instrument 910 and surgical consumable 920, respectively. By radio frequency identification, the two flexible RFID tags 901, 901a carry information about the surgical instrument 910 and surgical consumable 920, such as the type, manufacturing date, and transportation process/date of the surgical instrument 910 and surgical consumable 920. The information is entered into the flexible RFID tags 901, 901a with an external computer 800. However, the information is not limited thereto but is subject to changes as needed. Furthermore, the number of the flexible RFID tags is not limited thereto but is subject to changes as needed, for example, is changed to at least one, so as to correspond in quantity to the surgical instrument and surgical consumable. The operating radio frequency of the flexible RFID tags 901, 901a falls within a high frequency range of 3 M~30 MHz. As revealed by experimental data, radio frequency which falls within a high frequency range penetrates the human body effectively without affecting the human body. In an embodiment, the operating radio frequency of the flexible RFID tags 901, 901a is 13.56 MHz, as required by ISM (Industrial Scientific Medical), at a read distance of around 1.5 m. The number of the flexible RFID tags 901, 901a is not limited to two but is subject to changes as needed, for example, is changed to at least one, so as to correspond in quantity to the surgical instrument 910 and surgical consumable 920. The external computer 800 is, for example, a host computer in a surgical central control room. The external computer 800 is connected to an external blockchain network, such that a surgical procedure is thoroughly recorded, and the record is not to be tampered with, so as to achieve decentralization and protect the rights and interests of surgeons and patients.

The surgical item managing system 1 for a smart operating room includes a scanner 20, a warning module 30, a network module 40, a blockchain tracking module 50, a processing module 60, a memory 70 and a video recording module 80. As shown in FIG. 1 and FIG. 3, in an embodiment of the present disclosure, the scanner 20 is a scanning platform equipped with a built-in RFID tag reader/writer, lies 1-5 m above the operating table 200, and faces the operating table 200 to scan the flexible RFID tags 901, 901a and receive return signals from the flexible RFID tags 901, 901a. After that, the return signals are transmitted to the processing module 60, such that the positions of the flexible RFID tags 901, 901a can be computed subsequently. The scanner 20 has a plurality of read regions 21. Each read region 21 has positioning coordinates (X, Y), where X is A to H corresponding to the read regions from bottom to top, and Y is 1 to 4 corresponding to the read regions from left to right. After the scanner 20 has scanned the flexible RFID tags 901, 901a, the scanned flexible RFID tags 901, 901a transmit the return signals to the read regions 21 of the scanner 20. Owing to unequal distances between the flexible RFID tags 901, 901a, the level of signal strength of the received return signals varies from read region 21 to read region 21. For example, the read region 21 with positioning coordinates (E, 3) is nearest to the flexible RFID tag 901, and thus the level of signal strength of the received return signals from the flexible RFID tag 901 is the highest. For example, the read regions 21 with positioning coordinates (E, 2), (E, 4), (D, 3), (F, 3), which lie in the vicinity of the read region 21 with positioning coordinates (E, 3), are far from the flexible RFID tag 901, and thus the level of signal strength of the received return signals is low. Data about the levels of signal strength of the return signals received by the read regions 21 is sent to the processing module 60, such that the processing module 60 computes the position of the flexible RFID tag 901 according to different levels of signal strength. If none of the flexible RFID tags 901, 901a lies on the operating table 200, the flexible RFID tags will be scanned by the read regions 21 but with an overly low level of signal strength; alternatively, the flexible RFID tags may not even be scanned, and it can be determined that none of the flexible RFID tags lies on the operating table 200 and inside the body of the patient 100 either.

In an embodiment of the present disclosure, the warning module 30 is, for example, a warning lamp disposed at the scanner 20 and in signal connection with the scanner 20. The warning module 30 gives a light warning when the scanner 20 determines that the position of any one of the flexible RFID tags 901, 901a is in the body of the patient 100. However, the warning module 30 may also be any other warning apparatus, for example, a player capable of generating a warning sound.

In an embodiment of the present disclosure, the network module 40 is a network card disposed at the scanner 20 and in signal connection with the scanner 20. The network module 40 transmits data about the positions of the flexible RFID tags 901, 901a to the external computer 800. The external computer 800 connects to the network module 40 and controls the surgical item managing system 1.

In an embodiment of the present disclosure, the blockchain tracking module 50 is disposed at the scanner 20 and in signal connection with the scanner 20. The blockchain tracking module 50 is a computing chip in signal connection with an external blockchain network 700. The blockchain tracking module 50 records a transportation history of the flexible RFID tags 901, 901a in the external blockchain network 700. The record of the transportation history of the flexible RFID tags 901, 901a includes place of surgery, and the process of preserving and transporting the surgical instrument 910 and surgical consumable 920 of the surgical item 900. Caretakers enter data about the transportation history of the flexible RFID tags 901, 901a into the blockchain tracking module 50 with the external computer 800. Then, the blockchain tracking module 50 records the transportation history in the external blockchain network 700. Therefore, with a blockchain capable of tracking and its record being unlikely to be tampered with, the transportation history of the surgical instrument 910 and surgical consumable 920 of the surgical item 900 can be clearly recorded and managed.

In an embodiment of the present disclosure, the processing module 60 is, for example, a CPU (central processing unit). The processing module 60 is disposed at the scanner 20 and in signal connection with the scanner 20, warning module 30, network module 40, blockchain tracking module 50, memory 70 and video recording module 80. The processing module 60 coordinates and controls the operation of the scanner 20, warning module 30, network module 40, blockchain tracking module 50, memory 70 and video recording module 80. The processing module 60 computes the positions of the flexible RFID tags 901, 901a according to the levels of signal strength of the return signals and determines whether the positions of the flexible RFID tags 901, 901a and the position of the patient 100 overlap, so as to determine whether the positions of the flexible RFID tags 901, 901a are in the body of the patient 100.

In an embodiment of the present disclosure, the memory 70 is in signal connection with the processing module 60. The memory 70 stores data and software required to perform the surgical item managing method for a smart operating room. The video recording module 80 is a photographic lens disposed at the scanner 20 and adapted to take images of the patient 100, so as to obtain a position of the patient 100.

As shown in FIG. 1 through FIG. 4, in an embodiment of the present disclosure, the surgical item managing method for a smart operating room is programmed to become a computer program software stored in the memory 70. When a surgeon has carried out an operation to the patient 100 on the operating table 200 to such an extent that a suturing process is going to be performed, a nurse connects the external computer 800 to the surgical item managing system 1, such that the surgical item managing system 1 executes the software of the surgical item managing method, so as to prevent the surgical item 900 from being left behind in the body of the patient 100. After that, the surgical item managing system 1 performs step 101: scanning flexible RFID tags and receiving a plurality of return signals.

In an embodiment of the present disclosure, the read regions 21 of the scanner 20 above the operating table 200 face the operating table 200 so as to scan the flexible RFID tags 901, 901a. The flexible RFID tags 901, 901a thus scanned transmit return signals to the read regions 21 of the scanner 20. With the flexible RFID tags 901, 901a being different in position, the read regions 21 obtain different levels of signal strength.

Then, the surgical item managing system 1 performs step 102: computing positions of the flexible RFID tags according to levels of signal strength of return signals.

The data about levels of signal strength of the return signals received by the read regions 21 is transmitted to the processing module 60, such that the processing module 60 computes the position of the flexible RFID tag 901 according to different levels of signal strength. In this embodiment, the level of signal strength of the return signals received by read region 21 with positioning coordinates (E, 3) from the flexible RFID tag 901 is the highest, whereas the levels of signal strength of the return signals received by read regions 21 with positioning coordinates (E, 2), (E, 4), (D, 3), (F, 3), which lie in the vicinity of read region 21 with positioning coordinates (E, 3), are low. Thus, data about different levels of signal strength of the return signals received by the read regions 21 is transmitted to the processing module 60, such that the processing module 60 determines that read region 21 with positioning coordinates (E, 3) is nearest to the flexible RFID tag 901 according to different levels of signal strength, so as to compute and confirm that the position of the flexible RFID tag 901 lies below read region 21 with positioning coordinates (E, 3).

Then, the surgical item managing system 1 performs step 103: taking images of a patient, so as to obtain a position of the patient.

The video recording module 80 takes images of the patient 100 on the operating table 200, so as to obtain an image of a position of the patient 100. The image taken of the position of the patient 100 by the video recording module 80 is transmitted to the processing module 60. The video recording module 80 shoots a video of the entire surgical procedure and takes pictures thereof at important points in time during the surgical procedure and uploads the video and pictures to a blockchain network for evidential purposes.

Then, the surgical item managing system 1 performs step 104: determining whether the positions of the flexible RFID tags and the position of the patient overlap, so as to determine whether the positions of the flexible RFID tags are in the patient's body.

The processing module 60 computes the position of the flexible RFID tag 901 according to different levels of signal strength and receives the image of the position of the patient 100 from the video recording module 80. After that, the processing module 60 compares the position of the flexible RFID tag 901 and the image (sent from the video recording module 80) of the position of the patient 100 to determine whether the position of the flexible RFID tag 901 and the position of the body of the patient 100 overlap. If they overlap, it will confirm that the position of the flexible RFID tag 901 is in the patient's body. If they do not overlap, it will confirm that the position of the flexible RFID tag 901 is not in the patient's body.

Upon determination that the position of the flexible RFID tag 901 is not in the patient's body, the surgeon performs a suturing process on the body of the patient 100 to finalize the surgical operation and terminate the process flow of the method. Upon determination that the position of the flexible RFID tag 901 is in the patient's body, the surgical item managing system 1 performs step 105: giving a warning.

The processing module 60 sends the message of determining that the position of the flexible RFID tag 901 is in the patient's body to the warning module 30 to cause the warning module 30 to give a light warning and thus instantly warn the surgeon of the presence of the surgical instrument 910 with the flexible RFID tag 901 in the body of the patient 100. Therefore, the surgeon removes the surgical instrument 910 with the flexible RFID tag 901 from the body of the patient 100 before performing the suturing process on the body of the patient 100.

Then, the surgical item managing system 1 performs step 106: transmitting data about the positions of the flexible RFID tags to an external computer.

After computing the position of the flexible RFID tag 901, the processing module 60 transmits data about the position of the flexible RFID tag 901 to the network module 40. The network module 40 transmits the data about the position of the flexible RFID tag 901 to the external computer 800. Then, the position of the flexible RFID tag 901 is recorded in the external computer 800 to serve as surgical reference data.

Finally, the surgical item managing system 1 performs step 107: recording transportation history in a blockchain network.

The nurse operates the external computer 800, such that the external computer 800 enters the transportation history of the flexible RFID tags 901, 901a into the blockchain tracking module 50. Then, the blockchain tracking module 50 records the transportation history of the flexible RFID tags 901, 901a in the external blockchain network 700. With a blockchain being capable of tracking item transportation history, a process of preservation and transportation and the place of surgery corresponding to the surgical instrument 910 and surgical consumable 920 of the surgical item 900 are recorded in the external blockchain network 700. Consequently, with a blockchain capable of tracking and its record being unlikely to be tampered with, the transportation history of the surgical instrument 910 and surgical consumable 920 of the surgical item 900 can be clearly recorded and managed.

The present disclosure provides the surgical item managing system 1 and surgical item managing method to prevent a surgeon from leaving a surgical item behind in a patient's body at the end of a surgical operation which the surgeon has performed on the patient, so as to enhance medical safety. Furthermore, the surgical item managing system 1 and surgical item managing method are effective in tracking surgical item transportation history. Part of the surgical item is made of biodegradable plastic and thus is environment-friendly.

What is claimed is:

1. A surgical item managing method for a smart operating room, for use by a surgical item managing system for the smart operating room to manage a surgical item used during a surgical procedure, the surgical item comprising a flexible RFID tag, the surgical item managing method comprising the steps of:
    obtaining a tag position of the flexible RFID tag;
    taking an image of a patient, so as to obtain an image position of the patient;
    determining whether a position of the flexible RFID tag and the image position of the patient overlap, so as to determine whether the surgical item corresponding to the flexible RFID tag is in the patient's body; and
    giving a warning if the surgical item is in the patient's body.

2. The surgical item managing method for a smart operating room according to claim 1, wherein the surgical item managing system for the smart operating room further comprises a scanner, and the scanner comprises a plurality of read regions, wherein the step of obtaining the tag position of the flexible RFID tag further comprises: scanning the flexible RFID tag with the scanner and receiving a plurality of return signals from the flexible RFID tag by the plurality of read regions.

3. The surgical item managing method for a smart operating room according to claim 2, wherein the step of obtaining the tag position of the flexible RFID tag further comprises: computing the tag position of the flexible RFID tag according to levels of signal strength of the return signals received by the read regions.

4. The surgical item managing method for a smart operating room according to claim 3, wherein the read region which receives the return signals with the highest level of signal strength is nearest to the flexible RFID tag.

5. The surgical item managing method for a smart operating room according to claim 4, further comprising: transmitting data about the position of the flexible RFID tag to an external computer.

6. The surgical item managing method for a smart operating room according to claim 5, further comprising: recording in a blockchain network a transportation history carried by the flexible RFID tag.

7. A surgical item managing system for a smart operating room, the surgical item managing system being adapted to manage a surgical item used during a surgical procedure, the surgical item comprising a flexible RFID tag, the surgical item managing system comprising:
    a scanner for scanning the flexible RFID tag, so as to obtain a tag position of the flexible RFID tag;
    a video recording module for taking an image of a patient, so as to obtain an image position of the patient;
    a processing module in signal connection with the scanner and the video recording module and adapted to obtain a position of the flexible RFID tag according to a data which the scanner acquires by scanning the flexible RFID tag and determine whether a position of the flexible RFID tag and the image position of the patient overlap, so as to determine whether the surgical item corresponding to the flexible RFID tag is in the patient's body; and
    a warning module in signal connection with the processing module and adapted to generate a warning signal when the processing module confirms presence of the surgical item in the patient's body.

8. The surgical item managing system for a smart operating room according to claim 7, wherein the scanner comprises a plurality of read regions for receiving a plurality of return signals from the flexible RFID tag.

9. The surgical item managing system for a smart operating room according to claim 8, wherein the processing module computes the tag position of the flexible RFID tag according to levels of signal strength of the return signals received by the read regions.

10. The surgical item managing system for a smart operating room according to claim 9, wherein the read region which receives the return signals with the highest level of signal strength is nearest to the flexible RFID tag.

11. The surgical item managing system for a smart operating room according to claim 10, further comprising a network module in signal connection with the scanner and adapted to transmit to an external computer a data about the position of the flexible RFID tag.

12. The surgical item managing system for a smart operating room according to claim 11, further comprising a blockchain tracking module in signal connection with the scanner and adapted to record in a blockchain network a transportation history carried by the flexible RFID tag.

13. The surgical item managing system for a smart operating room according to claim 12, wherein the surgical item further comprises at least one surgical instrument and at least one surgical consumable.

* * * * *